(12) United States Patent
Kamba et al.

(10) Patent No.: US 8,269,967 B2
(45) Date of Patent: Sep. 18, 2012

(54) METHOD FOR MEASURING CHARACTERISTIC OF OBJECT TO BE MEASURED, STRUCTURE CAUSING DIFFRACTION PHENOMENON, AND MEASURING DEVICE

(75) Inventors: Seiji Kamba, Nagaokakyo (JP); Takashi Kondo, Nagaokakyo (JP); Koji Tanaka, Nagaokakyo (JP); Kazuhiro Takigawa, Nagaokakyo (JP); Yuichi Ogawa, Sendai (JP)

(73) Assignees: Murata Manufacturing Co., Ltd., Nagaokakyo-Shi, Kyoto-fu (JP); National University Corporation Tohoku University, Sendai-shi, Miyagi (JP)

( * ) Notice: Subject to any disclaimer, the term of this patent is extended or adjusted under 35 U.S.C. 154(b) by 0 days.

(21) Appl. No.: 13/239,830

(22) Filed: Sep. 22, 2011

(65) Prior Publication Data
US 2012/0008142 A1    Jan. 12, 2012

Related U.S. Application Data

(63) Continuation of application No. PCT/JP2010/055344, filed on Mar. 26, 2010.

(30) Foreign Application Priority Data

Mar. 27, 2009 (JP) ................................. 2009-080107

(51) Int. Cl.
  *G01J 3/28* (2006.01)
(52) U.S. Cl. ........................................................ 356/328
(58) Field of Classification Search .................. 356/328, 356/432
  See application file for complete search history.

(56) References Cited

U.S. PATENT DOCUMENTS

| | | | |
|---|---|---|---|
| 5,973,316 | A | 10/1999 | Ebbesen et al. |
| 6,052,238 | A | 4/2000 | Ebbesen et al. |
| 6,236,033 | B1 | 5/2001 | Ebbesen et al. |
| 7,435,385 | B2 | 10/2008 | Lin et al. |
| 2002/0127565 | A1 | 9/2002 | Cunningham et al. |
| 2003/0017580 | A1 | 1/2003 | Cunningham et al. |
| 2003/0017581 | A1 | 1/2003 | Li et al. |

(Continued)

FOREIGN PATENT DOCUMENTS

JP    11-072607 A    3/1999
(Continued)

OTHER PUBLICATIONS

Hisa Yoshida, et al.; "Label-free detection of protein using a metallic mesh," IEICE Technical Report, Nov. 20, 2007, vol. 107, No. 355, pp. 99 to 102.

(Continued)

*Primary Examiner* — Roy M Punnoose
(74) *Attorney, Agent, or Firm* — Dickstein Shapiro LLP (57) ABSTRACT

A method of attaching an object to be measured to a structure causing a diffraction phenomenon; irradiating the structure to which the object to be measured is attached and which causes the diffraction phenomenon with an electromagnetic wave; detecting the electromagnetic wave scattered by the structure causing the diffraction phenomenon; and measuring a characteristic of the object to be measured from the frequency characteristic of the detected electromagnetic wave. The object to be measured is attached directly to the surface of the structure causing the diffraction phenomenon. Thus, the method for measuring the characteristic of an object to be measured exhibits an improved measurement sensitivity and high reproducibility. A structure causing a diffraction phenomenon and used for the method, and a measuring device are provided.

21 Claims, 8 Drawing Sheets

U.S. PATENT DOCUMENTS

| | | |
|---|---|---|
| 2003/0132392 A1 | 7/2003 | Kuroda et al. |
| 2004/0132172 A1 | 7/2004 | Cunningham et al. |
| 2007/0196043 A1 | 8/2007 | Peled et al. |
| 2008/0246970 A1 | 10/2008 | Kuroda et al. |
| 2009/0310133 A1* | 12/2009 | Ogino et al. .................. 356/310 |
| 2010/0025586 A1 | 2/2010 | Ogawa et al. |

FOREIGN PATENT DOCUMENTS

| | | |
|---|---|---|
| JP | 2003270132 A | 9/2003 |
| JP | 2004-070288 A | 3/2004 |
| JP | 2004529324 A | 9/2004 |
| JP | 2007-232456 A | 9/2007 |
| JP | 2007537439 A | 12/2007 |
| JP | 2008-185552 A | 8/2008 |

OTHER PUBLICATIONS

International Search Report, mailed Jun. 29, 2010.

PCT Written Opinion in PCT/JP2010/055344, mailed Jun. 29, 2010.

* cited by examiner

METHOD FOR MEASURING CHARACTERISTIC OF OBJECT TO BE MEASURED, STRUCTURE CAUSING DIFFRACTION PHENOMENON, AND MEASURING DEVICE

This is a continuation of application Ser. No. PCT/JP2010/055344, filed Mar. 25, 2010, the entire contents of which are incorporated herein by reference.

TECHNICAL FIELD

The present invention relates to a method for measuring a characteristic of an object to be measured by disposing the object to be measured on a structure causing a diffraction phenomenon, irradiating the structure on which the object to be measured is disposed, causing a diffraction phenomenon with an electromagnetic wave and analyzing a scattering spectrum thereof in order to analyze a characteristic of a substance, as well as a structure causing a diffraction phenomenon and a measuring device employed therefor.

BACKGROUND ART

In order to analyze a characteristic of a substance, a method for measuring a characteristic of the object to be measured by disposing the object to be measured on a void-disposed structure, irradiating the void-disposed structure on which the object to be measured is disposed with an electromagnetic wave and analyzing a transmission spectrum thereof is employed in general. More specifically, a technique of irradiating an object to be measured such as protein attached to a metal mesh filter with a terahertz wave and analyzing a transmission spectrum can be listed, as an example.

As a prior art of such a technique of analyzing a transmission spectrum with an electromagnetic wave, Patent Document 1 discloses a method constituted of a void-disposed structure (metal mesh, for example) having a void region, an object to be measured being held on a plane of the void-disposed structure, an electromagnetic wave irradiation portion applying an electromagnetic wave toward the object to be measured and an electromagnetic wave detection portion measuring the electromagnetic wave transmitted through the void-disposed structure for measuring a characteristic of the object to be measured on the basis of that the electromagnetic wave projected from the electromagnetic wave irradiation portion toward the void-disposed structure is inclinatorily incident upon the plane including the void region and the position of a dip waveform caused in a frequency characteristic of a measured value moves due to the presence of the object to be measured. As specific methods for holding the object to be measured on the plane of the void-disposed structure, only a method for sticking a support film of polyamide resin or the like to the surface of the void-disposed structure and attaching the object to be measured to the support film and a method for measuring a fluid or a substance dispersed in the fluid by employing an airtight or liquid-tight container in place of the support film are disclosed (Japanese Patent Laying-Open No. 2008-185552: Examples 1 to 3 of Patent Document 1, FIGS. 3, 6 and 10, paragraphs [0017] and [0018]).

In a case of holding the object to be measured on the void-disposed structure through the support film or the like as specifically described in Japanese Patent Laying-Open No. 2008-185552 (Patent Document 1), however, the frequency characteristic of the measured value changes due to the degree of adhesion between the void-disposed structure and the support film or deflection. Further, there has been such a problem that the frequency characteristic is dispersed due to dispersion (thickness dispersion, permittivity dispersion) of the support film itself, to cause dispersion in the measured value.

SUMMARY OF INVENTION

Technical Problem

In consideration of the aforementioned circumstances, an object of the present invention is to provide a method for measuring a characteristic of an object to be measured which improves measuring sensitivity and has high reproducibility, as well as a structure causing a diffraction phenomenon and a measuring device employed therefor.

Solution to Problem

The present invention provides a measuring method, comprising:

attaching an object to be measured to a structure causing a diffraction phenomenon;

irradiating the aforementioned structure to which the aforementioned object to be measured attaches, causing a diffraction phenomenon with an electromagnetic wave;

detecting the electromagnetic wave scattered in the aforementioned structure causing a diffraction phenomenon; and measuring a characteristic of the aforementioned object to be measured from a frequency characteristic of the detected electromagnetic wave, and characterized in that the aforementioned object to be measured is directly attached to the surface of the aforementioned structure causing a diffraction phenomenon.

In the present invention, the aforementioned object to be measured is preferably directly attached to the surface of the aforementioned structure causing a diffraction phenomenon by chemical bonding.

Preferably, at least a partial surface of the aforementioned structure causing a diffraction phenomenon is made of a conductor.

Preferably, a host molecule for attaching the aforementioned object to be measured is bonded to at least a partial surface of the aforementioned structure causing a diffraction phenomenon, and the aforementioned object to be measured is directly attached to the aforementioned structure causing a diffraction phenomenon by the host molecule. More preferably, the aforementioned host molecule is bonded to at least a partial surface of the aforementioned structure causing a diffraction phenomenon by chemical bonding.

Preferably, the aforementioned host molecule is a molecule specifically attaching the object to be measured. Preferably, a plurality of species of host molecules for attaching different types of objects to be measured are bonded to at least a partial surface of the aforementioned structure causing a diffraction phenomenon.

The present invention also relates to a structure causing a diffraction phenomenon employed for the aforementioned measuring method, in which at least a partial surface of the aforementioned structure causing a diffraction phenomenon is made of a conductor, and/or a host molecule for attaching the aforementioned object to be measured is bonded to at least a partial surface of the aforementioned structure causing a diffraction phenomenon.

Further, the present invention also relates to a measuring device measuring the characteristic of the aforementioned object to be measured, including:

the aforementioned structure causing a diffraction phenomenon, an irradiation source irradiating the aforementioned structure to which the aforementioned object to be measured attaches, causing a diffraction phenomenon with an electromagnetic wave, and a detection portion detecting the electromagnetic wave emitted from the aforementioned irradiation portion and scattered in the aforementioned structure to which the aforementioned object to be measured attaches, causing a diffraction phenomenon.

Advantageous Effects of Invention

According to the present invention, the object to be measured is so directly disposed on the surface of the structure causing a diffraction phenomenon where measuring sensitivity is improved, and dispersion in measurement is so suppressed that measurement having high reproducibility can be performed.

BRIEF DESCRIPTION OF DRAWINGS

FIGS. 2(a) and 2(b) are diagrams for illustrating a structure causing a diffraction phenomenon employed in a first embodiment of the present invention, where

FIGS. 3(a) and 3(b) are diagrams for illustrating a structure causing a diffraction phenomenon employed in a second embodiment of the present invention in which

DESCRIPTION OF EMBODIMENTS

The structure causing a diffraction phenomenon employed in the present invention, while not particularly restricted so far as the same is a structure causing a diffraction phenomenon when irradiated with an electromagnetic wave, is preferably a quasi-periodic structure or a periodic structure. A quasi-periodic structure denotes a structure not having translation symmetry but keeping order in arrangement. As quasi-periodic structures, a Fibonacci structure and a Penrose structure can be listed as a one-dimensional quasi-periodic structure and a two-dimensional quasi-periodic structure respectively, for example. The periodic structure denotes a structure having spatial symmetry represented by translation symmetry, and can be classified into a one-dimensional periodic structure, a two-dimensional periodic structure and a three-dimensional structure in response to the dimensions of the symmetry. As one-dimensional periodic structures, a wire grid structure, a one-dimensional diffraction grating and the like can be listed, for example. As two-dimensional periodic structures, a metal mesh, a two-dimensional diffraction grating and the like can be listed, for example. Among these periodic structures, the two-dimensional periodic structure is preferably employed.

Figure 1:
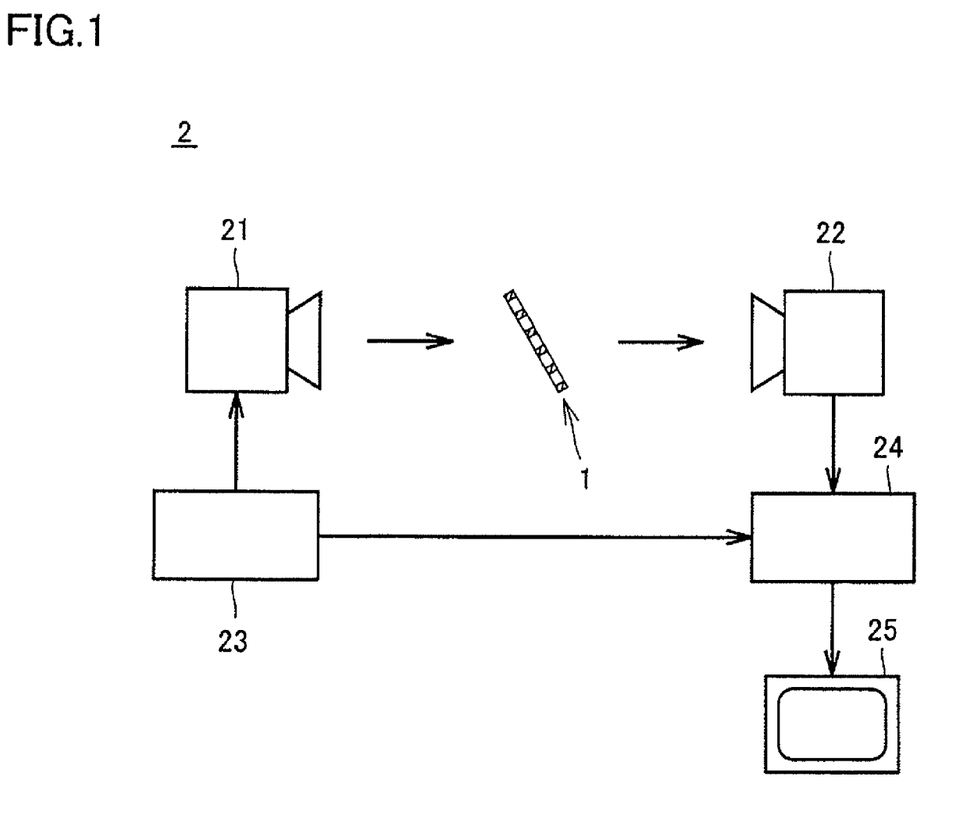
FIG. 1 is a schematic diagram for illustrating a measuring method and a measuring device according to the present invention.

An example of the measuring method according to the present invention is now described with reference to FIG. 1. FIG. 1 is a diagram schematically showing the overall structure of a measuring device 2 according to the present invention and configuration of a structure 1 causing a diffraction phenomenon in measuring device 2. As shown in FIG. 1, measuring device 2 includes an irradiation portion 21 generating an electromagnetic wave and applying the same to structure 1 causing a diffraction phenomenon, and a detection portion 22 detecting the electromagnetic wave scattered in structure 1. Measuring device 2 also includes an irradiation control portion 23 controlling the operation of irradiation portion 21, an analytic processing portion 24 analyzing a detection result of detection portion 22 and a display portion 25 displaying an analytical result of analytical processing portion 24. Irradiation control portion 23 may be connected also to analytical processing portion 24, in order to synchronize timing of detection. In the present invention, "scatter" denotes a wide concept including transmission as one form of forward scattering and reflection as one form of backward scattering.

In aforementioned measuring device 2, irradiation portion 21 generates (radiates) an electromagnetic wave under the control of irradiation control portion 23. The electromagnetic wave radiated from irradiation portion 21 is applied to structure 1, and the electromagnetic wave scattered in structure 1 causing a diffraction phenomenon is detected by detection portion 22. The electromagnetic wave detected by detection portion 22 is transferred to analytic processing portion 24 as an electric signal, and displayed on display portion 25 in a form visible as a frequency characteristic of transmittance, for example.

In measuring device 2, structure 1 is generally obliquely disposed with respect to the direction of incidence of the electromagnetic wave, and the angle (incident angle) formed by a normal direction of structure 1 causing a diffraction phenomenon of measuring device 2 and the direction of incidence of the electromagnetic wave is preferably 1 to 89°, and more preferably 5 to 15°. A characteristic of an object to be measured can be measured on the basis that the position of a dip waveform in a frequency characteristic measured value changes due to the presence of the object.

The electromagnetic wave employed in the present invention is not particularly restricted so long as the same is an electromagnetic wave capable of causing a diffraction phenomenon in response to the structure of the structure causing a diffraction phenomenon but any of an electric wave, an infrared ray, a visible ray, an ultraviolet ray, an X-ray, a γ-ray and the like can be used, and the frequency thereof is not particularly restricted either, but preferably 1 GHz to 1 PHz. As a specific electromagnetic wave, a terahertz wave generated from a light source of a short beam pulse laser by an optical rectification effect of an electrooptical crystal such as ZnTe, an infrared ray radiated from a high-pressure mercury lamp or a ceramic lamp or a visible ray emitted from a semiconductor laser can be listed, for example.

To measure the characteristic of the object to be measured is to perform a determination of a compound employed as the object to be measured or various types of qualitative analyses, and the case of measuring the content of a small quantity of the object in a solution or the like or performing identification of the object can be listed, for example. More specifically, the method can be, for example, dipping the structure in a solution in which the object to be measured is dissolved, washing away solvent or excess object to be measured, drying the structure and thereafter measuring the characteristic of the object with the aforementioned measuring device.

The measuring method according to the present invention is characterized in that the object to be measured is directly attached to the structure causing a diffraction phenomenon. In the present invention, to directly attach the object to be measured to the structure causing a diffraction phenomenon includes not only the case where chemical bonding or the like is directly formed between the surface of the structure causing a diffraction phenomenon and the object to be measured, but also the case where the object to be measured is bonded to a host molecule previously bonded to the surface of the structure causing a diffraction phenomenon. However, the case where the object to be measured is attached to a member such as a support film separately provided in contact with the structure causing a diffraction phenomenon as in the prior art is not included. Thus, the object to be measured is so directly attached to the surface of the structure causing a diffraction phenomenon that measuring sensitivity improves as compared with the prior art in which the object is attached to the separately provided member such as a support film. Further, the measurement dispersion is so suppressed that a measurement having high reproducibility can be performed.

In the present invention, the object to be measured is preferably directly attached to the structure causing a diffraction phenomenon by chemical bonding. In general, a step of bringing the surface of the structure causing a diffraction phenomenon into contact with a solution containing the object to be measured by dipping or the like for attaching the object to be measured and subsequently washing excess solvent or unattached object is required. This is in order that the object to be measured attaching to the structure causing a diffraction phenomenon does not desorb through such a step.

First Embodiment

This embodiment is characterized in that a structure causing a diffraction phenomenon in which at least a partial surface is made of a conductor is employed in the aforementioned method for measuring a characteristic of an object to be measured. The structure causing a diffraction phenomenon employed in this embodiment is a structure 1 having a plurality of void portions 11 formed at regular intervals, as shown in a perspective view of FIG. 2(a) and a sectional view of FIG. 2(b). While at least the partial surface of structure 1 causing a diffraction phenomenon denotes at least a partial surface of any of a major surface 10a, side surfaces 10b and void portion side surfaces 11a shown in FIG. 2(a), at least a partial surface of major surface 10a is preferably made of a conductor.

It is assumed that the conductor employed in this embodiment denotes an object (substance) conducting electricity, and includes not only a metal but also a semiconductor. As the metal, a metal capable of bonding to a functional group of a compound having a functional group such as a hydroxy group, a thiol group or a carboxyl group, or a metal whose surface can be coated with a functional group such as a hydroxy group or an amino group can be suitably employed, and an alloy of such a metal can also be employed. Gold, silver, copper, iron, nickel, chromium, silicon, germanium or the like can be listed as the metal, which is preferably gold, silver, copper, nickel or chromium, and more preferably gold. In a case of employing either gold or nickel, a thiol group can be advantageously bonded to the surface of the structure causing a diffraction phenomenon particularly when the object to be measured has the thiol group (—SH group). In a case of employing nickel, the corresponding functional group can be advantageously bonded to the surface of the structure causing a diffraction phenomenon particularly when the object to be measured has a hydroxy group (—OH) or a carboxyl group (—COOH).

As the semiconductor, a semiconductor compound such as a group IV semiconductor (Si, Ge or the like), a group II-VI semiconductor (ZnSe, CdS, ZnO or the like), a group III-V semiconductor (GaAs, InP, GaN or the like), a group IV compound semiconductor (SiC, SiGe or the like) or a group I-III-VI semiconductor ($CuInSe_2$ or the like) or an organic semiconductor can be listed, for example.

Figures 2A, 2B:
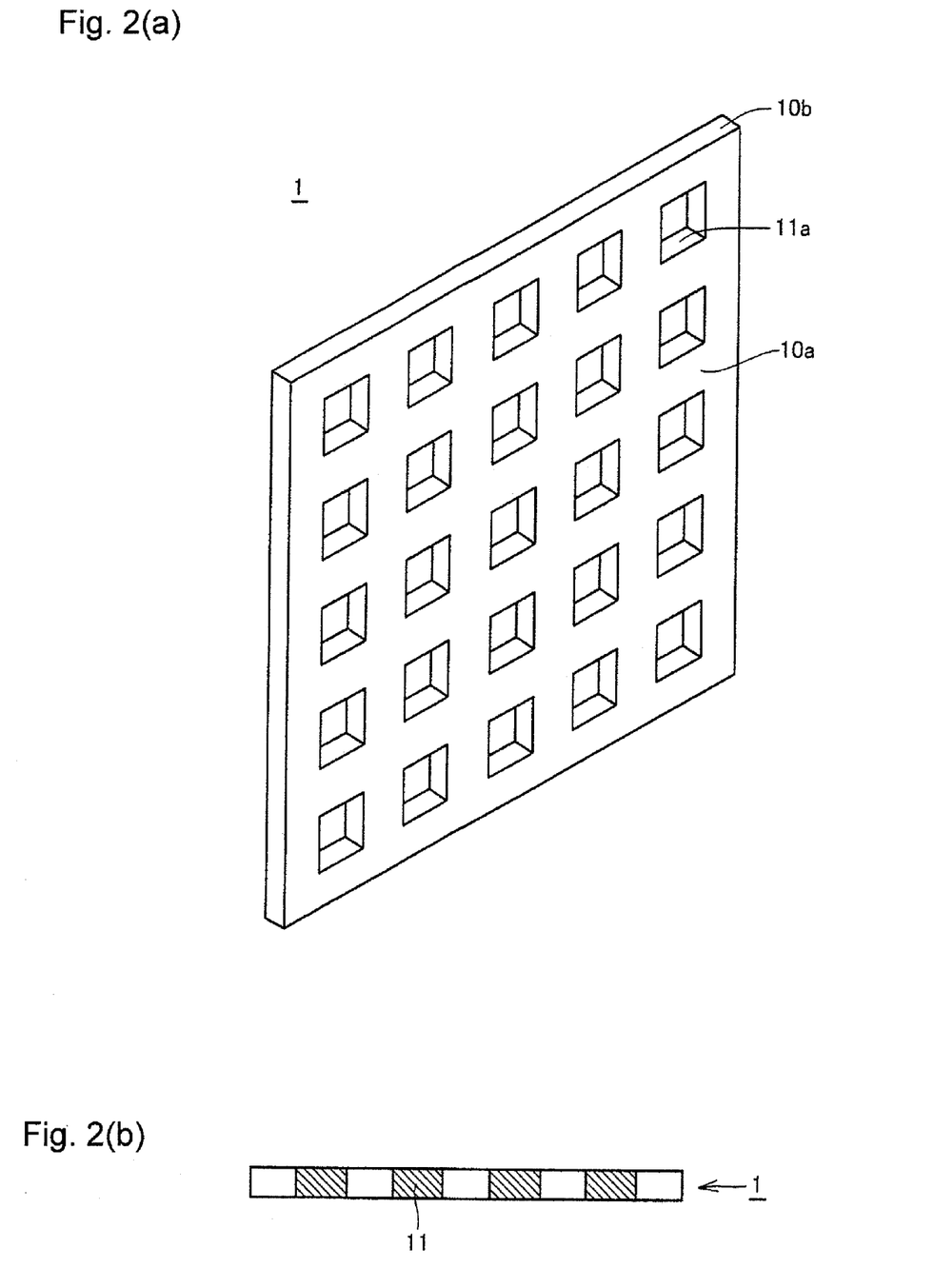
FIG. 2(a) is a perspective view of the structure causing a diffraction phenomenon.
FIG. 2(b) is a schematic sectional view thereof.

While the structure causing a diffraction phenomenon in this embodiment has the plurality of void portions formed at the regular intervals, the shape of the structure causing the diffraction phenomenon is not particularly restricted. Further, the configuration of the void portions is not restricted to the matrix configuration shown in FIG. 2 either, so long as the void portions are regularly or periodically arranged. In addition, the number of the void portions is not restricted either, so far as one or more void portions are provided. Therefore, wide-ranging materials and wide-ranging structures can be selected as the structure causing a diffraction phenomenon in response to the type of the object to be measured, measurement conditions and the like.

Figure 4:
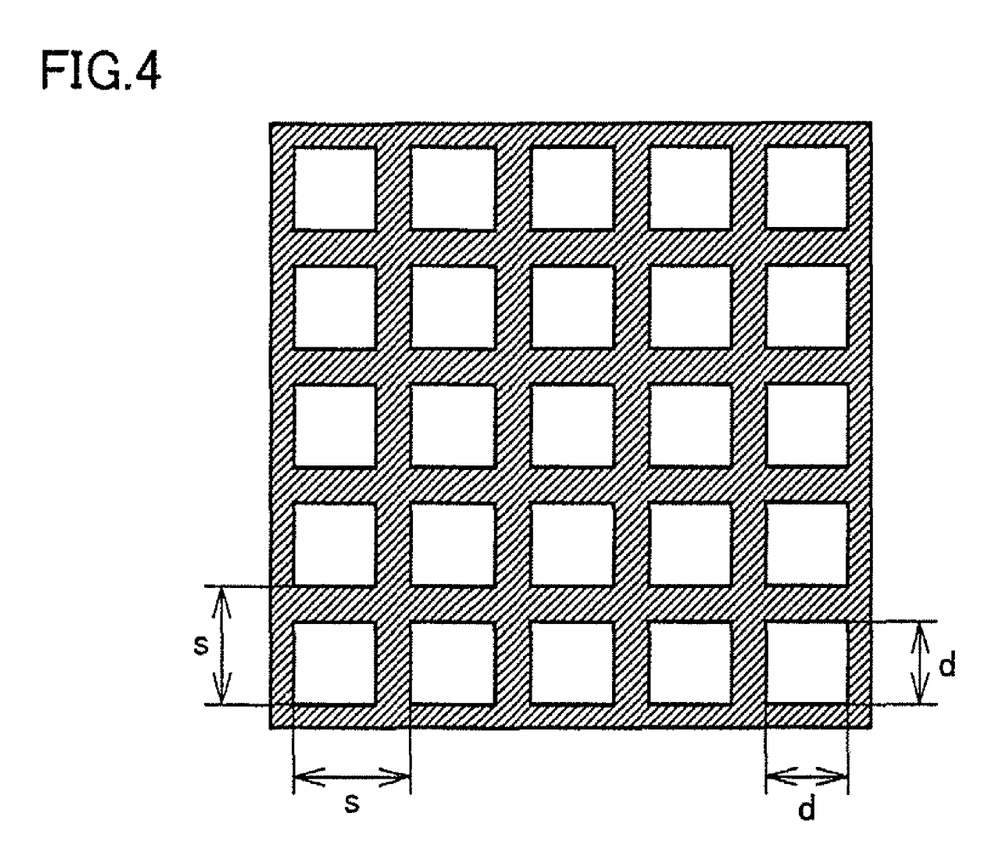
FIG. 4 is a schematic diagram for illustrating a lattice structure of a structure (metal mesh) causing a diffraction phenomenon employed in the present invention.

While the size of the void portions of the structure causing a diffraction phenomenon is properly designed in response to the measuring method, the material for and the characteristic of the structure causing a diffraction phenomenon, the frequency of the used electromagnetic wave and the like, and it is difficult to generalize the range thereof, the grating space of the void portions shown with "s" in FIG. 4 is preferably at least 1/10 and not more than 10 times the wavelength of the electromagnetic wave employed for the measurement. If the grating space "s" of the void portions is out of this range, it is hard to cause the diffraction phenomenon. As the pore size of the void portions, a pore size of the void portions shown with "d" in FIG. 4 is preferably at least 1/10 and not more than 10 times the wavelength of the electromagnetic wave employed for the measurement. If the pore size of the void portions is out of this range, the strength of the forwardly scattering electromagnetic wave so weakens that it is difficult to detect the signal.

While the thickness of the structure causing a diffraction phenomenon is properly designed in response to the measuring method, the material for and the characteristic of the structure causing a diffraction phenomenon, the frequency of the used electromagnetic wave and the like, and it is difficult to generalize the range thereof, the thickness is preferably not more than several times the wavelength of the electromagnetic wave employed for the measurement in a case of detecting the forwardly scattering electromagnetic wave. If the thickness of the structure enlarges beyond this range, the strength of the forwardly scattering electromagnetic wave so weakens that it is difficult to detect the signal.

In this embodiment, the chemical bonding in the case where the object to be measured is attached to the structure causing a diffraction phenomenon by the chemical bonding is not particularly restricted so long as the same is such that the object to be measured does not easily desorb from the structure causing a diffraction phenomenon in processing in the measurement. Covalent bonding (covalent bonding between a metal and a thiol group, for example), van der Waals bonding, ionic bonding, metallic bonding, hydrogen bonding or the like can be preferably listed, and covalent bonding is more preferable among these, form the viewpoint that bonding strength between the object to be measured and the structure causing a diffraction phenomenon is large.

Second Embodiment

This embodiment is characterized in that an object to be measured is directly bonded to the surface of a structure causing a diffraction phenomenon by previously bonding host molecules for attaching the object to be measured to at least a partial surface of the structure causing a diffraction phenomenon and attaching the object to these host molecules in the aforementioned method for measuring a characteristic of an object to be measured.

Figure 3A:
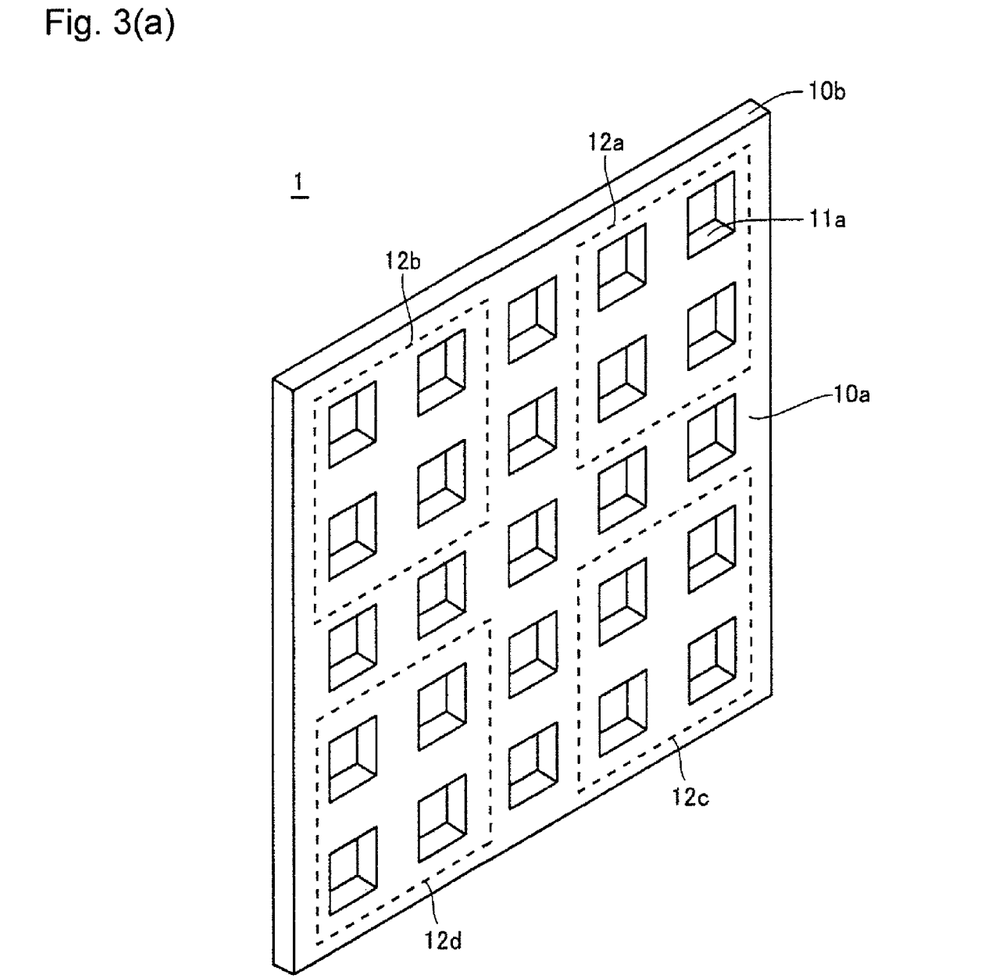
FIG. 3(a) is a perspective view of the structure causing a diffraction phenomenon.
Figure 3B:
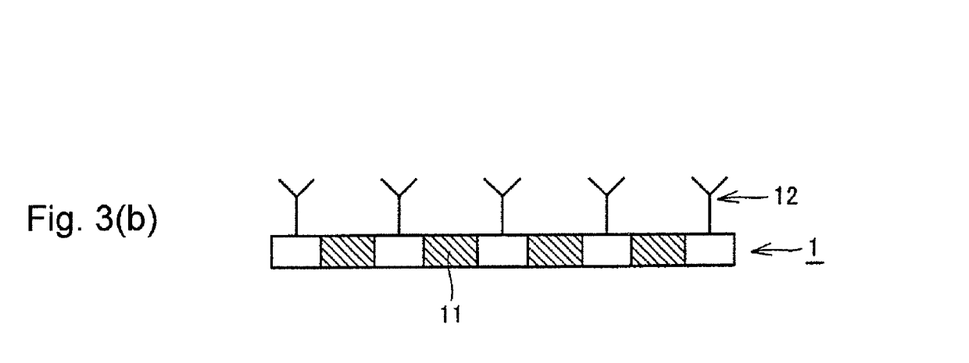
FIG. 3(b) is a schematic sectional view thereof.

The structure causing a diffraction phenomenon employed in this embodiment is described with reference to a perspective view of FIG. 3(a) and a sectional view of FIG. 3(b). In this embodiment, host molecules 12 are bonded to at least a partial surface of a structure 1 causing a diffraction phenomenon, having a plurality of void portions 11 formed at regular intervals. While at least the partial surface denotes at least a partial surface of any of a major surface 10a, side surfaces 10b and void portion side surfaces 11a shown in FIG. 3(a), the host molecules 12 are preferably bonded to at least a partial surface of major surface 10a.

In this embodiment, a plurality of species of host molecules for attaching different types of objects to be measured may be bonded to the at least a partial surface of the structure causing a diffraction phenomenon. More specifically, in host molecule bond regions 12a, 12b, 12c and 12d on the surface of structure 1 shown in FIG. 3(a), different types of host molecules may be bonded to the respective regions, for example. Thus, a plurality of species of host molecules are so bonded to one structure so that characteristics of different types of objects to be measured can be simultaneously measured in single measurement. If there is a guest (object to be measured) corresponding to at least one of the plurality of species of host molecules, the same can be detected as a spectrum change shown in FIG. 8. Further, the type of guest molecules in a detected image clarifies by which host molecule bond region a camera-detected image of a transmitted electromagnetic wave corresponds.

The host molecules employed in this embodiment are those capable of attaching the object to be measured. The host molecules, which are not particularly restricted, are preferably those capable of specifically bonding the object to be measured. As to the relation between the host molecules capable of specifically attaching the object to be measured and the object to be measured, an antigen and an antibody, a sugar chain and protein, lipid and protein, a low-molecular compound (ligand) and protein, protein and protein, single-strand DNA and single-strand DNA or the like can be listed, and when either one of these two having specific affinity is the object to be measured, the other one can be employed as the host molecules. In other words, the antibody can be employed as the host molecules if the antigen is the object to be measured, while the antigen can be employed as the host molecules if the antibody is the object to be measured to the contrary. Such host molecules capable of specifically attaching the object to be measured are so employed that measuring sensitivity for the object to be measured can be increased.

While the aforementioned structure to which the host molecules are bonded causing a diffraction phenomenon may be a structure in which at least a partial surface is made of a conductor as that employed in the first embodiment or may be another structure causing a diffraction function whose surface is not made of a conductor, the material for the surface of the structure causing a diffraction phenomenon is properly selected in response to bondability of the used host molecules.

According to the present invention, the host molecules are preferably bonded to the surface of the structure causing a diffraction phenomenon by chemical bonding. In general, a step of bringing the surface of the structure causing a diffraction phenomenon into contact with a solution containing the object to be measured by dipping or the like for attaching the object to be measured, subsequently washing off excess solvent or unattached object and drying the same is required. This is in order that the host molecules bonded to the structure causing a diffraction phenomenon do not desorb along with the object to be measured through such a step.

While the present invention is now described in more detail with reference to Examples, the present invention is not restricted to these.

EXAMPLES

Example 1

In this Example, a metal mesh, having tetragonal-lattice-arrayed square pores as shown in a schematic diagram of FIG. 4, entirely made of Ni was used as a structure causing a diffraction phenomenon. The grating space ("s" in FIG. 4), pore size ("d" in FIG. 4) and thickness of this metal mesh are 63.5 μm, 45 μm and 8 μm, respectively, and the shape of the whole is a discoidal shape of 50 mm in diameter. Measurement of an object to be measured prepared from bovine serum albumin was performed with such a metal mesh.

First, an aqueous 0.1 weight % bovine serum albumin solution was directly applied to the surface of the metal mesh with an ink jet printer. Droplets of one shot (=14 pL) per 35.5 μm square were discharged from the ink jet printer, and wet-on-wet coating was performed while controlling the shot number, thereby controlling the quantity of the aqueous bovine serum albumin solution applied onto the metal mesh to be 5.6 ng/mm$^2$ or 11.2 ng/mm$^2$. This metal mesh coated with the aqueous bovine serum albumin solution was naturally dried in a drying container overnight. Three samples of metal meshes coated with the same quantity of bovine serum albumin were prepared for each quantity.

Figure 5:
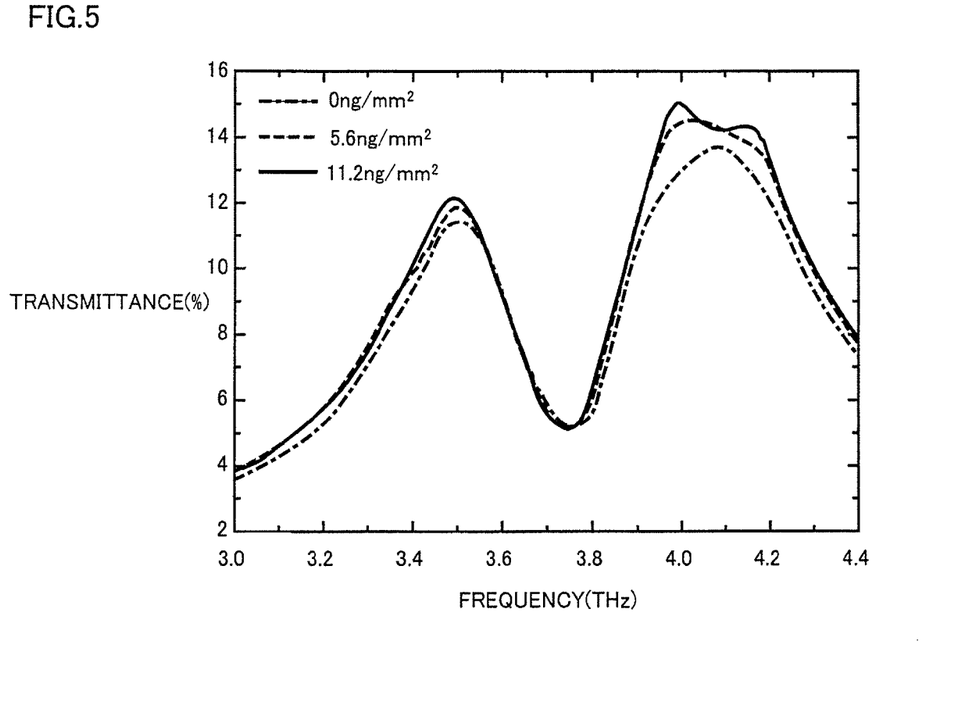
FIG. 5 is a graph showing transmission spectra in Example 1.

After confirming that the surface of each metal mesh was dry, the transmission spectrum of the metal mesh coated with bovine serum albumin was measured. Far-infrared FT-IR was employed for the measurement, while a high-pressure mercury lamp and a deuterated triglycine sulfate detector (DTGS) were employed as a light source and a detector respectively. The measurement was performed as to each sample with frequency resolution of 60 GHz and an integration frequency of 1000 times. As contrast, three metal meshes were prepared and subjected to measurement similarly as to metal meshes coated with pure water in place of the aqueous bovine serum albumin solution (i.e., quantity of application of bovine serum albumin: 0 ng/mm$^2$). FIG. 5 shows the average of the measurement results of the three metal meshes coated with the same quantity of bovine serum albumin as to each quantity.

As shown in FIG. 5, difference in transmission spectra is clearly observed in the cases where the quantities of bovine serum albumin per unit area of the surfaces of the metal meshes are 0 ng/mm$^2$, 5.6 ng/mm$^2$ and 11.2 ng/mm$^2$, and it is understood that the quantities of bovine serum albumin on the surfaces of the metal meshes can be determined/measured by this measurement of these transmission spectra.

Figure 6:
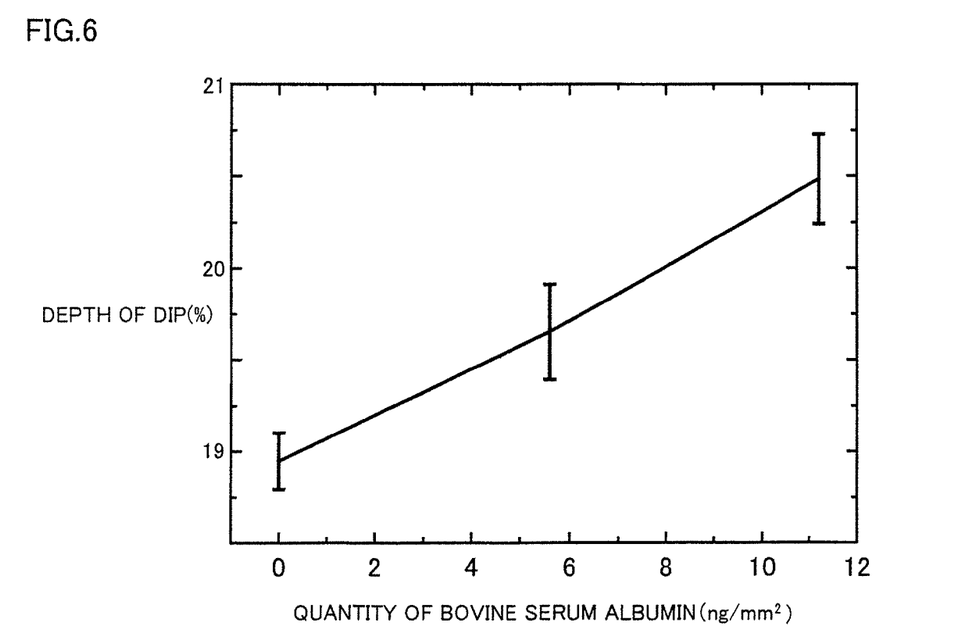
FIG. 6 is a graph showing the depths of dips in the respective transmission spectra of FIG. 5.

FIG. 6 is a graph showing the relation between the quantities of application of bovine serum albumin on the surfaces of the metal meshes (quantities of bovine serum albumin per unit area) and the depths of dip waveforms (difference between transmittance at 3.50 THz and transmittance at 3.75 THz in FIG. 5. unit: %) in the transmission spectra of FIG. 5.

As shown in FIG. 6, a significant difference is obtained in the depths of the dip waveforms in the cases where the quantities of bovine serum albumin per unit area of the surfaces of the metal meshes are 0 ng/mm$^2$, 5.6 ng/mm$^2$ and 11.2 ng/mm$^2$, and it is understood that the quantities of bovine serum albumin on the surfaces of the metal meshes can be determined/measured from these measured values of the depths of the dip waveforms.

The measuring method according to the present invention is capable of measurement at the ng/mm$^2$ level, and is excellent in measuring sensitivity. This is conceivably because it was possible to remove a noise factor resulting from a support film by easily bringing the object to be measured into contact with the metal mesh with no deflection and holding the same.

The transmission spectra in this Example were measured with such an electromagnetic wave incident from an oblique direction that an angle (incident angle) formed by the normal direction of structure 1 and the direction of incidence of the electromagnetic wave was 10°.

Example 2

In this Example, two metal meshes having tetragonal-lattice-arrayed square pores as shown in the schematic diagram of FIG. 4, whose surfaces were plated with gold were prepared as structures causing diffraction phenomena. The grating space ("s" in FIG. 4), pore size ("d" in FIG. 4) and thickness of each metal mesh are 260 μm, 182 μm and 60 μm, respectively, and the shape of the whole is a discoidal shape of 50 mm in diameter. Measurement of a substance to be measured prepared from a sugar chain polymer having a thiol group (mannose polymer to which a thiol group was added) was performed with such a metal mesh.

Figure 7:
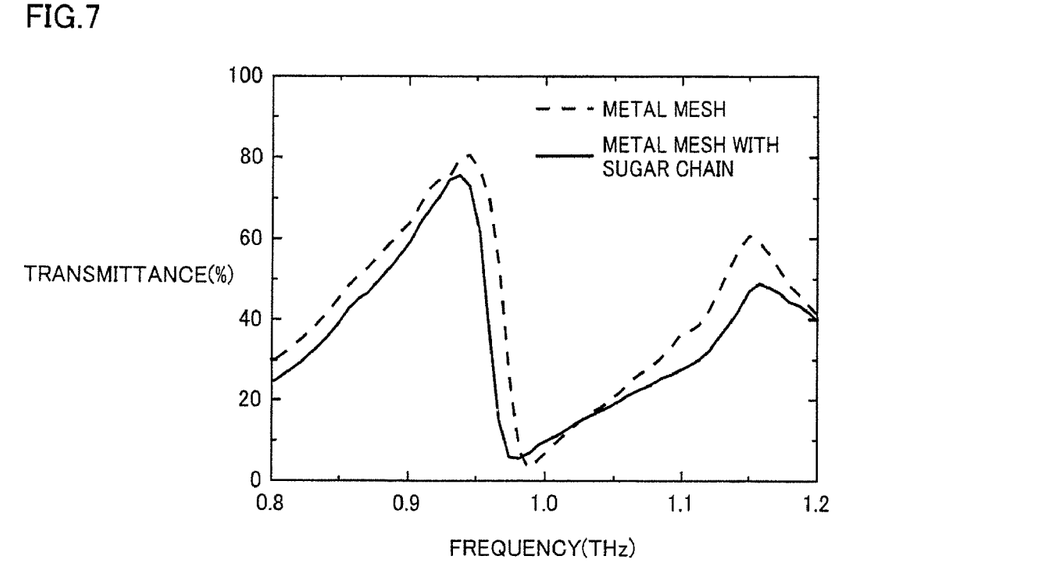
FIG. 7 is a graph showing transmission spectra in Example 2.

First, the metal mesh was dipped in 10 mL of an aqueous solution (concentration: 0.5 mg/mL) of a mannose polymer having a thiol group (content of the thiol group was 0.17 to 0.66% per unit weight of the mannose polymer having the thiol group) overnight, washed with pure water, and naturally dried in a drying container for about one hour, for uniformly fixing the mannose polymer onto the metal mesh. As to the metal mesh to which the sugar chain polymer was fixed, the transmission spectrum was measured with a time domain terahertz spectroscopic system (THz-TDS). The measurement was performed with frequency resolution of 7 GHz. As contrast, a metal mesh dipped in pure water in place of the aqueous sugar chain polymer solution was also prepared, and a transmission spectrum was similarly measured. FIG. 7 shows the transmission spectra obtained by the measurement.

In the transmission spectra shown in FIG. 7, it is understood that the sugar chain polymer is attached onto the metal mesh so that the transmission spectrum shifted toward a low-frequency side and it was possible to measure the presence of the sugar chain polymer compared with the case of only the metal mesh. For example, the frequency at which transmittance minimized shifted from 0.99 THz to 0.97 THz due to the presence of the sugar chain polymer.

The transmission spectra in this Example were measured with such an electromagnetic wave incident from an oblique direction that an angle (incident angle) formed by the normal direction of metal mesh 1 and the direction of incidence of the electromagnetic wave was 10°.

Example 3

In this Example, measurement of an object to be measured prepared from lectin (ConA) was performed by employing a metal mesh to whose surface a sugar chain polymer (mannose polymer having a thiol group) was fixed as a structure to which host molecules were bonded causing a diffraction phenomenon, similarly to Example 2.

Figure 8:
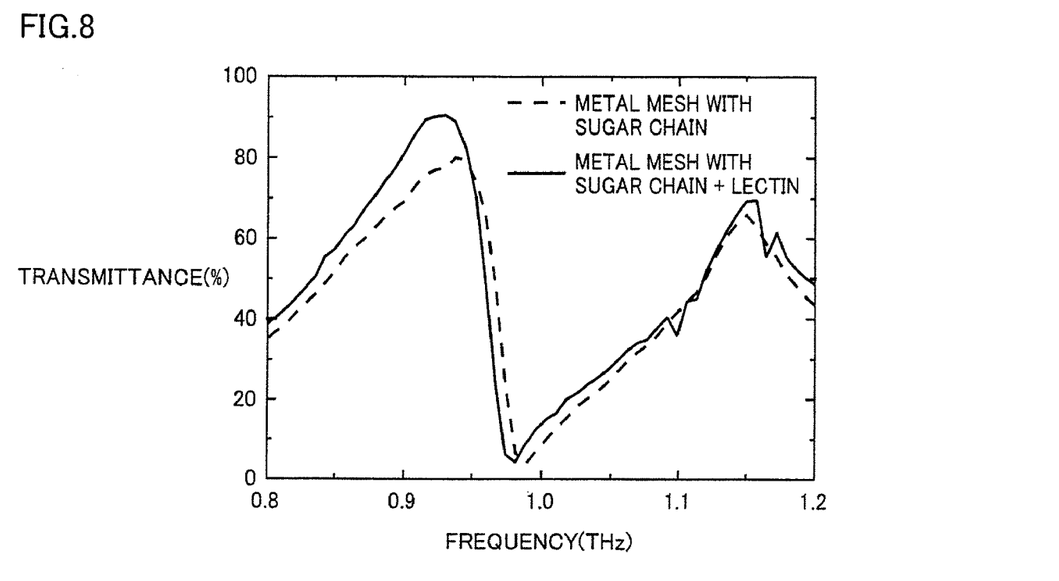
FIG. 8 is a graph showing transmission spectra in Example 3.

First, the metal mesh to which the sugar chain polymer was fixed was dipped in 5 mL of an aqueous lectin (ConA) solution having a concentration of 1 mg/mL for four hours to attach lectin to the sugar chain polymer which were host molecules. Thereafter the metal mesh was washed with pure water to wash off unattached lectin away, and naturally dried in a drying container for about one hour. The transmission spectrum was measured on the dried metal mesh to which lectin was fixed similarly to Example 2. As contrast, a transmittance spectrum of the metal mesh to which the sugar chain polymer was fixed before the dipping in the aqueous lectin solution was also similarly measured beforehand. FIG. 8 shows the transmission spectra obtained by the measurement.

It is understood that the transmission spectrum ("metal mesh with sugar chain+lectin" in FIG. 8) of the metal mesh to which lectin attached shifted to a low-frequency side and it was possible to measure the presence or absence of lectin as compared with the transmission spectrum ("metal mesh with sugar chain" in FIG. 8) of the metal mesh before the dipping in the aqueous lectin solution. In other words, lectin was so fixed that the depth (difference in transmittance at 0.93 THz and transmittance at 0.98 THz in FIG. 8. unit: %) of a dip waveform increased from 80% to 90%.

The transmission spectra in this Example were measured with such an electromagnetic wave incident from an oblique direction that an angle (incident angle) formed by the normal direction of metal mesh 1 and the direction of incidence of the electromagnetic wave was 10°.

Reference Example

A simulation calculation for illustrating that a frequency characteristic of a measured value changes and dispersion is caused in the measured value in a case of holding an object to be measured on a void-disposed structure through a support film or the like, due to the degree of adhesion of the void-disposed structure and the support film or deflection.

Figure 9:
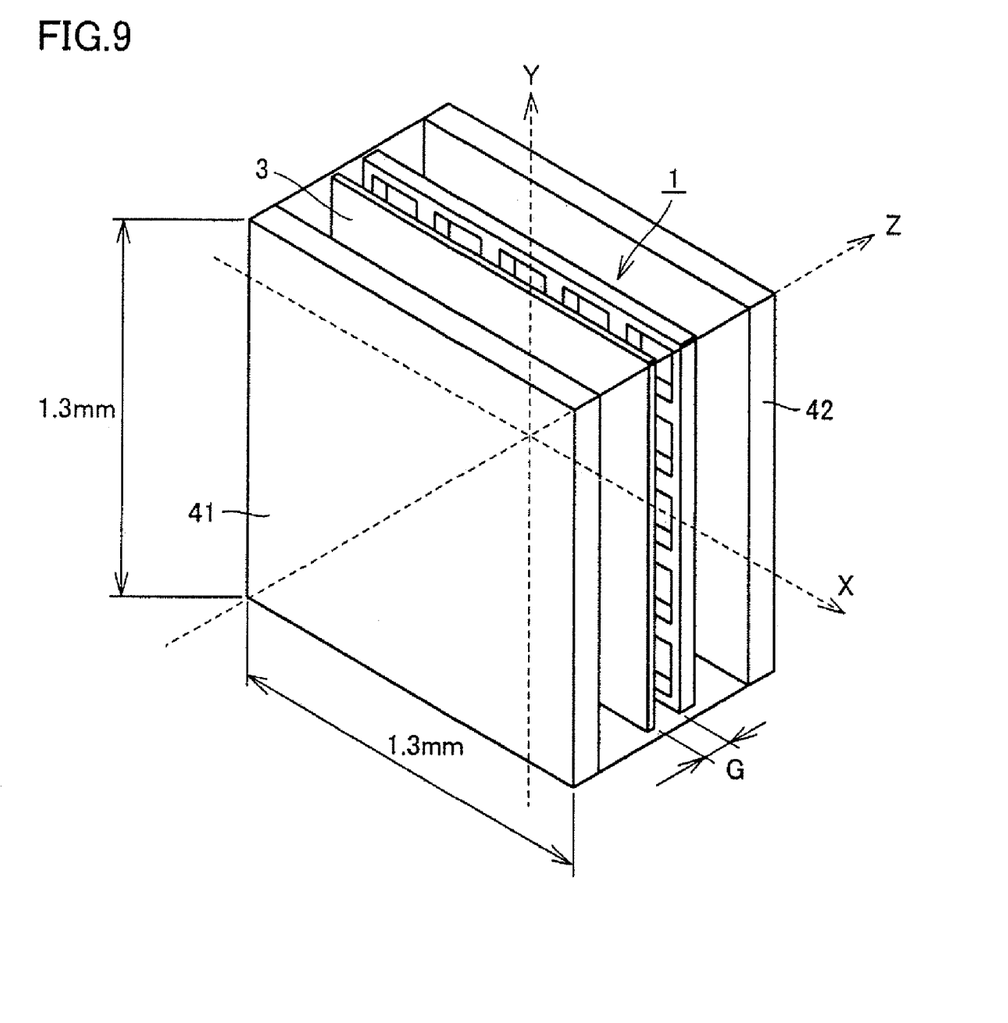
FIG. 9 is a schematic diagram for illustrating reference example.

More specifically, an electromagnetic field simulation was executed with respect to a virtual model of a type holding an object to be measured on a void-disposed structure through a support film or the like as shown in FIG. 9. Referring to FIG. 9, a structure 1 causing a diffraction phenomenon and a support film 3 are set between two ports 41 and 42 at an interval of a distance G, and the distance between port 41 and support film 3 is 280 μm. The distance between port 42 and structure 1 causing a diffraction phenomenon is 315 μm. Structure 1 causing a diffraction phenomenon is a metal mesh having a pore size of 180 μm, a grating space of 254 μm and a thickness of 60 μm, and support film 3 is a dielectric film ($\varepsilon r = 1.5$, tan δ=0) having a thickness of 25 μm. Ports 41 and 42 are in shapes having major surfaces of 1.3 mm square.

An electromagnetic field simulation in a case of setting the distance G between aforementioned structure 1 causing a diffraction phenomenon and support film 3 to 0 μm, 50 μm, 100 μm, 200 μm and 400 μm was performed to calculate transmittance spectra. The calculation was performed on the assumption that periodic boundary conditions were satisfied in directions X and Y and the major surface of metal mesh 1 was substantially equal to the size of the major surfaces of ports 41 and 42.

Figure 10A:
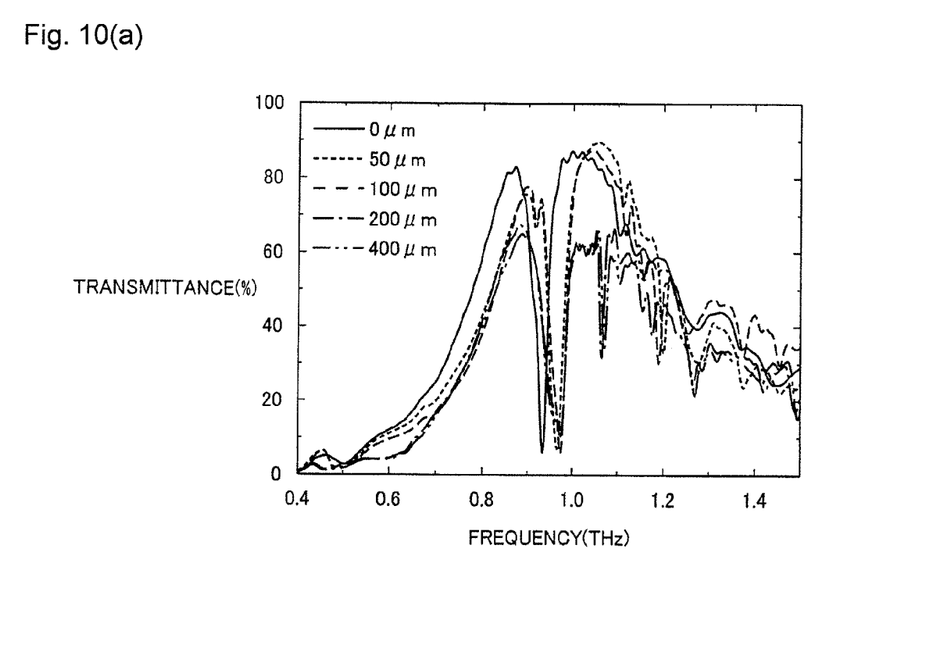
FIGS. 10(a) and 10(b) are graphs showing transmission spectra in reference example.
Figure 10B:
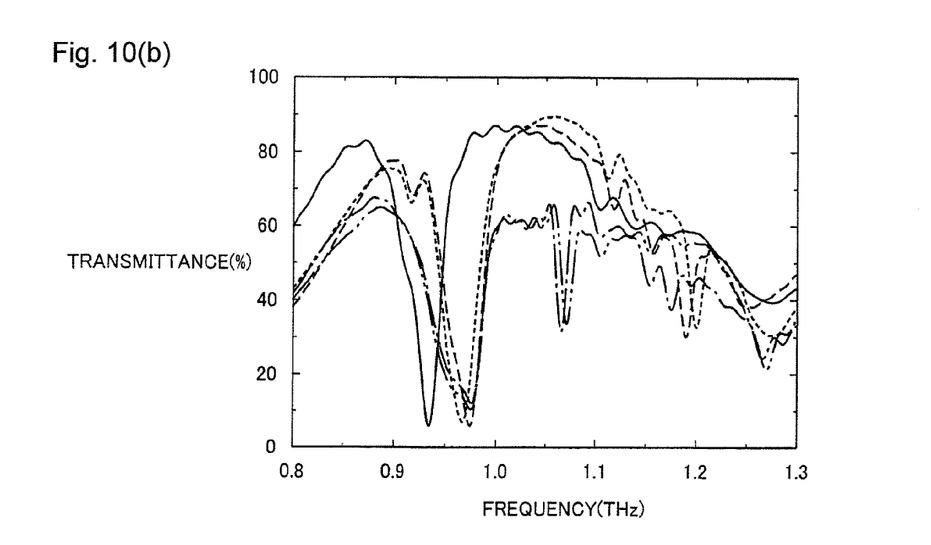

FIG. 10(*a*) shows the obtained transmittance spectra. FIG. 10(*b*) shows spectra obtained by enlarging the transmittance spectra in a portion of 0.8 to 1.3 THz in frequency in FIG. 10(*a*) in the horizontal direction. It is understood from FIG. 10 that the distance G between structure 1 causing a diffraction phenomenon and support film 3 so changes from 0 μm to 400 μm that the shapes of the transmittance spectra change. In particular, the change is most remarkable between the spectrum at the time when G was 0 μm (the state where the support film adhered to the metal mesh) and the spectrum at the time when G was 50 μm, and hence it is understood that the frequency characteristics of the measured values change due to the degree of adhesion of structure 1 causing a diffraction phenomenon and support film 3 or deflection, to cause dispersion in the measured values.

The transmission spectra in this reference example were measured with such an electromagnetic wave incident from an oblique direction that an angle (incident angle) formed by the normal direction of metal mesh 1 and the direction of incidence of the electromagnetic wave was 10°.

The embodiments and Examples disclosed this time must be considered as illustrative in all points and not restrictive. The range of the present invention is shown not by the above description but by the scope of claims for patent, and it is intended that all modifications within the meaning and range equivalent to the scope of claims for patent are included.

REFERENCE SIGNS LIST

1 structure causing diffraction phenomenon,
10*a* major surface,
10*b* side surface,
11 void portion,
11*a* void portion side surface,
12 antibody (host molecule),
12*a*, 12*b*, 12*c*, 12*d* host molecule bond region,
2 measuring device,
21 irradiation portion,
22 detection portion,
23 irradiation control portion,
24 analytical processing portion,
25 display portion,
3 support film,
41, 42 port.

The invention claimed is:

1. A measuring method, comprising:
attaching an object to be measured directly to a portion of a surface of a structure which causes a diffraction phenomenon, said structure having a plurality of void portions whose largest dimension is 1/10th to 10 times the wavelength of the measuring electromagnetic wave employed;
irradiating said structure with an electromagnetic wave;
detecting the electromagnetic wave scattered in said structure; and
measuring a characteristic of said object from a frequency characteristic of the detected electromagnetic wave.

2. The measuring method according to claim 1, wherein said object to be measured is directly attached to the surface of said structure by chemical bonding.

3. The measuring method according to claim 1, wherein at least a partial surface of said structure is made of a conductor.

4. The measuring method according to claim 3, wherein the conductor is a metal.

5. The measuring method according to claim 4, wherein the metal comprises gold.

6. The measuring method according to claim 1, wherein said object to be measured is directly attached to a host molecule which is directly attached to a partial surface of said structure.

7. The measuring method according to claim 6, wherein said host molecule is bonded to at least a partial surface of said structure by chemical bonding.

8. The measuring method according to claim 6, wherein said host molecule is a molecule specifically attaching to the object.

9. The measuring method according to claim 6, wherein a plurality of species of host molecules are bonded to at least a partial surface of said structure, and members of the species attach different types of objects to be measured.

10. A structure causing a diffraction phenomenon employed for the measuring method according to claim 1, comprising a structure having a plurality of void portions whose largest dimension is 1/10th to 10 times the wavelength of the measuring electromagnetic wave employed, in which at least a partial surface of said structure is made of a conductor and/or a host molecule for attaching said object to be measured is bonded thereto.

11. A measuring device for measuring a characteristic of an object to be measured, including:
the structure according to claim 10
an irradiation source disposed to irradiate said structure and cause a diffraction phenomenon with an electromagnetic wave; and
a detector disposed to detect the electromagnetic wave emitted from and scattered in the said structure.

12. The measuring method according to claim 1, wherein the structure is a two-dimensional periodic structure.

13. The measuring method according to claim 12, wherein the two-dimensional periodic structure is a grating having a plurality of pores whose largest dimension is 1/10th to 10 times the wavelength of the electromagnetic wave.

14. The measuring method according to claim 1, wherein the structure is obliquely disposed with respect to direct incidence of the electromagnetic wave.

15. The measuring method according to claim 14, wherein the angle of incidence is 1° to 89°.

16. The measuring method according to claim 14, wherein the angle of incidence is 5° to 15°.

17. The measuring method according to claim 16, wherein the structure is a two-dimensional periodic conductive structure.

18. The measuring method according to claim 17, wherein the two-dimensional periodic structure is a grating having a plurality of pores whose largest dimension is 1/10th to 10 times the wavelength of the electromagnetic wave.

19. The measuring method according to claim 18, wherein the structure comprises gold.

20. The measuring method according to claim 19, wherein said object to be measured is directly attached to the surface of said structure by covalent chemical bonding.

21. The measuring method according to claim 19, wherein said object to be measured is directed attached to a host molecule which is is directly attached to said structure.

* * * * *